United States Patent [19]

Henderson

[11] 4,448,884
[45] May 15, 1984

[54] GLASS-SURFACE MICROCARRIER FOR GROWTH OF CELL CULTURES

[75] Inventor: Timothy M. Henderson, Ann Arbor, Mich.

[73] Assignee: KMS Fusion, Inc., Ann Arbor, Mich.

[21] Appl. No.: 354,345

[22] Filed: Mar. 3, 1982

[51] Int. Cl.³ .......................... C12N 5/00; C12N 5/02; C12N 11/14
[52] U.S. Cl. .................................... 435/241; 435/176; 435/240; 502/439; 502/159
[58] Field of Search ........................ 435/240, 241, 176; 252/428, 449

[56] References Cited

U.S. PATENT DOCUMENTS

| | | | |
|---|---|---|---|
| 3,717,551 | 2/1973 | Bizzini et al. | 435/241 |
| 4,036,693 | 7/1977 | Levine et al. | 435/241 X |
| 4,177,253 | 12/1979 | Davies et al. | 435/176 X |
| 4,189,534 | 2/1980 | Levine et al. | 435/241 X |
| 4,266,032 | 5/1981 | Miller et al. | 435/241 |

OTHER PUBLICATIONS

Maissel et al., Handbook of Thin Film Technology, McGraw-Hill Book Co., NY, 1970, (pp.1–44).
"Cytodex TM", Beaded Microcarriers for Cell Culture, Pharmacia Fine Chemicals, Uppsala, Sweden, 1978, (p. 6).

Primary Examiner—David M. Naff
Attorney, Agent, or Firm—Barnes, Kisselle, Raisch, Choate, Whittemore & Hulbert

[57] ABSTRACT

A microcarrier for anchorage-dependent cell cultivation is prepared containing a spherical substrate of polymeric material having a bulk density of about 1 g/cc so as to be substantially buoyant in an aqueous culture medium, and a thin (less than 1 μm) coating layer of silicate glass. The silicate glass coating layer is preferably applied to a spherical precursor of polymeric material in an rf sputtering operation. An intermediate coating layer of magnetic material may be deposited prior to the silicate glass layer, so that the microcarriers may be readily removed from culture media by suitable subjection to a magnetic field.

7 Claims, No Drawings

GLASS-SURFACE MICROCARRIER FOR GROWTH OF CELL CULTURES

The present invention relates to microcarriers for growth of anchorage-dependent cell cultures. More particularly, the invention relates to glass-surface microspheres specifically adapted for use as such microcarriers, and to methods for manufacture of such microspheres.

BACKGROUND OF THE INVENTION

In the art of growing anchorage-dependent cell tissue cultures, it has heretofore been proposed to replace the standard roller bottles and petrie dishes with so-called microcarriers for providing enhanced surface area for cell attachment. The U.S. patent to Levine et al No. 4,189,534 proposes, for example, the microcarriers in the form of solid plastic beads be employed. It has been found, however, that plastic microcarriers of this type require alteration of electrically charged surface moieties to promote cell attachment, which alteration is difficult to control quantitatively in production and is toxic to some types of cell cultures if not properly controlled. It is also difficult to remove some cell types from the plastic bead surface.

It has also been proposed to employ solid glass beads as cell microcarriers. In addition to the aforementioned problems, a significant disadvantage of microcarriers previously proposed, including specifically solid beads of plastic or glass, is a difficulty in controlling or tailoring the density of the microcarrier to that of the selected culture medium. Conventional cell culture media are aqueous in nature and possess densities generally in the range of 1.03 to 1.09 g/cc. Silica glass beads, which possess desirable surface qualities, typically have a density on the order of 2.3 g/cc depending upon glass composition. To avoid settling and compaction of the microcarriers in the growth medium, which tends to inhibit cell growth, it is necessary to stir or otherwise continuously agitate the culture medium. However, vigorous agitation is itself destructive to many cell types. The art relating to microcarriers for animal cell cultures in general is reviewed in 3rd General Meeting of ESACT, Oxford 1979, *Develop, biol. Standard,* 46, pp, 109–294 (S. Karger, Basel 1980).

In the copending U.S. application of Downs et al, Ser. No. 332,377, filed Dec. 21, 1981 and assigned to the assignee hereof, the foregoing and other difficulties in the art are addressed by forming hollow glass precursor microspheres of silicate glass composition, and then tailoring the density of such precursor microspheres in a post-forming etching operation to match closely the density of the desired aqueous growth medium. This technique has proven successful in overcoming both the surface-charge and the buoyancy problems of the earlier art. However, the number of separate operations involved makes cost reduction desirable.

OBJECTS AND SUMMARY OF THE INVENTION

A general object of the present invention, therefore, is to provide a microcarrier having a density which closely matches that of typical cell culture media and embodies the desirable surface characteristics of silicate glass, but is less expensive to manufacture than are microcarriers previously proposed which embody similar benefits.

Another object of the present invention is to provide a microcarrier which may be readily removed from the culture media, and which is particularly well adapted for rapid removal using automated processes.

Another object of the invention is to provide a method of manufacturing such microcarriers.

Briefly stated, microcarriers are manufactured in accordance with one important aspect of the present invention by first fabricating a spherical precursor of polymeric material having a precursor bulk density substantially the same as that of the desired aqueous growth medium (about 1 g/cc), and then coating the polymeric precursor with a thin layer of silicate glass. The thin glass layer does not significantly alter the effective bulk density of the precursor, while imparting thereto the significant advantages of a glass attachment surface in terms of toxicity and ease with which cultures may be removed therefrom without significant damage. The microcarrier in accordance with the invention therefore comprises, and preferably consists essentially of, a neutral buoyancy (about 1 g/cc) spherical polymeric precursor and a thin (no greater than 1 μm) continuous surface coating of silicate glass.

In accordance with another important aspect of the present invention, microcarriers are provided with a composition consisting in part of magnetic material, whereby the microcarriers may be attracted by a magnetic field and readily removed from the culture medium. Preferably, such magnetic material comprises a thin coating of magnetic material deposited on the polymeric precursor in the foregoing discussion prior to deposition of the outer layer of silicate glass.

DESCRIPTION OF PREFERRED EMBODIMENTS

The spherical polymeric precursor may be formed by any conventional technique. For example, a film-forming polymer may be dissolved in a suitable solvent and then sprayed into the upper portion of a heated chamber or furnace in the form of atomized droplets. As the droplets fall by gravity within the heated chamber, the solvent rapidly evaporates and a polymeric skin or shell is formed. The U.S. patent to Veatch et al No. 2,797,201 discloses such a process and an apparatus for practicing such process. Nominal precursor size and density are controlled as a function of polymer/solvent concentration, drying temperature and droplet size. Droplets may typically be in the range of 5 to 500 microns in size. Drying temperatures may be in the range of 20° C. to 500° C. The product precursor may be collected dry at the bottom of the chamber, cleaned and sieve cut to the desired size range, such as the range of 106 to 200 microns.

The polymeric precursor may also be formed as solid beads by spraying and cooling molten polymers, directing a droplet generator or other conventional apparatus into a free-full zone such that the droplets are cooled and solidified during free-full and collected. Alternatively, solid pre-sized pieces (frit) of polymeric material may be fed into a tower furnace for melting and reforming as spherical beads during free-full.

The polymeric precursor material is selected to yield the desired bulk density at the desired size range, and for glass coatability. Polystyrene and polyethylene are examples of suitable materials. The precursor may be solid, hollow or porous. Depending upon the precursor material and the coating method to be employed, it may be desirable to surface-treat the precursor so as to render the same more susceptible to silicate glass coating. Precursor diameter in the range of 50 μm to 500 μm and density in the range of 1.00 to 1.10 g/cc are preferred.

Silicate glass coating of the polymeric precursor is preferably accomplished by rf sputter deposition. (The term "silicate glass" as used herein refers to a glass which includes oxides of silicon, with or without other metallic oxides.) Most preferably, a magnetron rf sputtering unit is employed to obtain a uniform coating around the spherical outer surface of the precursor without overheating the polymeric substrate. A coating thickness in the range of 300 Å to 1 μm has little measurable effect upon overall density and is suitable. A suitable magnetron rf sputtering unit is manufactured by Sloan Manufacturing Co. and designated Model No. S310. Another coating technique which may be employed is chemical vapor deposition.

The microcarriers of the present invention to the extent hereinabove described embody a number of significant advantages. Foremost is the fact that such microcarriers may be fabricated much less expensively than is the case with the all-glass microcarriers of the above-referenced copending application, while retaining the advantages which inhere in a glass surface for cell anchorage and an overall density which is suspendable in the culture medium—i.e. has neutral buoyancy in the selected medium. Additionally, the preferred rf sputter coating technique allows the glass composition to be readily varied, although high silica or pure silica glass are presently envisioned for most cell cultivation applications. The polymeric spherical substrate with the basic density of about 1 g/cc may, of course, be manufactured (or purchased) very inexpensively in a variety of sizes.

In accordance with a second important aspect of the present invention, an intermediate layer of magnetic material, such as a nickel coating, may be deposited on the polymeric substrate prior to deposition of the outer silicate glass layer. This is preferably accomplished in an rf sputtering operation as previously described. The magnetic material layer does not have any substantial effect upon microcarrier density. The microcarriers may then be readily removed from suspension in a culture medium, such as by insertion of a permanent magnet into the medium. In accordance with this aspect of the invention in its broadest aspects, the magnetic material may be otherwise included in the microcarrier, such as by occlusion within the polymeric substrate.

The invention claimed is:

1. A microcarrier adapted for use as growth sites for anchorage dependent cells in an aqueous cell culture medium comprising a spherical substrate of polymeric material having a density of about 1 g/cc and a thin continuous discrete surface layer of silicate glass composition entirely surrounding said substrate.

2. The microcarrier set forth in claim 1 wherein said substrate has a diameter in the range of 50 μm to 500 μm and a density in the range of 1.00 g/cc to 1.10 g/cc, and wherein said discrete surface layer has a thickness in the range of 300 Å to 1 μm.

3. The microcarrier set forth in claim 1 or 2 comprising a second discrete surface layer of magnetic material surrounding said substrate beneath said silicate glass layer.

4. A method of fabricating a microcarrier for anchorage-dependent cell cultivation comprising the steps of:
   (a) selecting a spherical precursor of polymeric material having a density of about 1 g/cc, and
   (b) depositing on said precursor a discrete continuous surface layer of silicate glass composition.

5. The method set forth in claim 4 wherein said step (b) is accomplished in an rf sputtering operation.

6. The method set forth in claim 4 or 5 comprising the additional step prior to said step (b) of:
   (c) depositing on said precursor a discrete surface layer of magnetic material, said layer of silicate glass composition being deposited over said layer of magnetic material.

7. The method set forth in claim 6 wherein said step (c) is accomplished in an rf sputtering operation.

* * * * *